United States Patent [19]

Maggard et al.

[11] Patent Number: 5,348,645

[45] Date of Patent: * Sep. 20, 1994

[54] DETERMINATION OF AROMATICS IN HYDROCARBONS BY NEAR INFRARED SPECTROSCOPY

[75] Inventors: Steven M. Maggard, Barboursville, W. Va.; William T. Welch, Ashland, Ky.

[73] Assignee: Ashland Oil, Inc., Ashland, Ky.

[*] Notice: The portion of the term of this patent subsequent to Sep. 8, 2009 has been disclaimed.

[21] Appl. No.: 942,117

[22] Filed: Sep. 8, 1992

Related U.S. Application Data

[60] Continuation-in-part of Ser. No. 839,982, Feb. 20, 1992, which is a division of Ser. No. 626,132, Dec. 11, 1990, Pat. No. 5,145,785.

[51] Int. Cl.$^5$ ............................................. C10G 45/00
[52] U.S. Cl. ..................................... 208/209; 208/12; 208/177; 208/DIG. 1; 436/55
[58] Field of Search ................... 208/177, 209, 208 R, 208/12; 436/55

[56] References Cited

U.S. PATENT DOCUMENTS

| | | | |
|---|---|---|---|
| 5,062,976 | 11/1991 | Audeh | 252/45 |
| 5,145,785 | 9/1992 | Maggard | 436/8 |
| 5,171,691 | 12/1992 | Kline et al. | 436/55 |

*Primary Examiner*—Helane Myers
*Attorney, Agent, or Firm*—Richard C. Willson, Jr.

[57] ABSTRACT

Mid-distillate hydrocarbon fuels, preferably having initial boiling points above 350° F., are separated e.g. by prep-HPLC into non-aromatic and aromatic fractions which are used to set 0% aromatics (the non-aromatics) and 100% aromatics (the aromatics) on an NIR spectrophotometer. From NIR aromatic band absorbances of unknown samples, their percent aromatics is determined using this two-point calibration and the Beer-Lambert equation. Preferred NIR bands of 1650-1700 and 2120-2256 exhibit excellent correlation with aromatics content. Also similar techniques measure sulfur through correlation with the benzothiophenic band and its overtones and combination bands, or possibly directly.

36 Claims, 10 Drawing Sheets

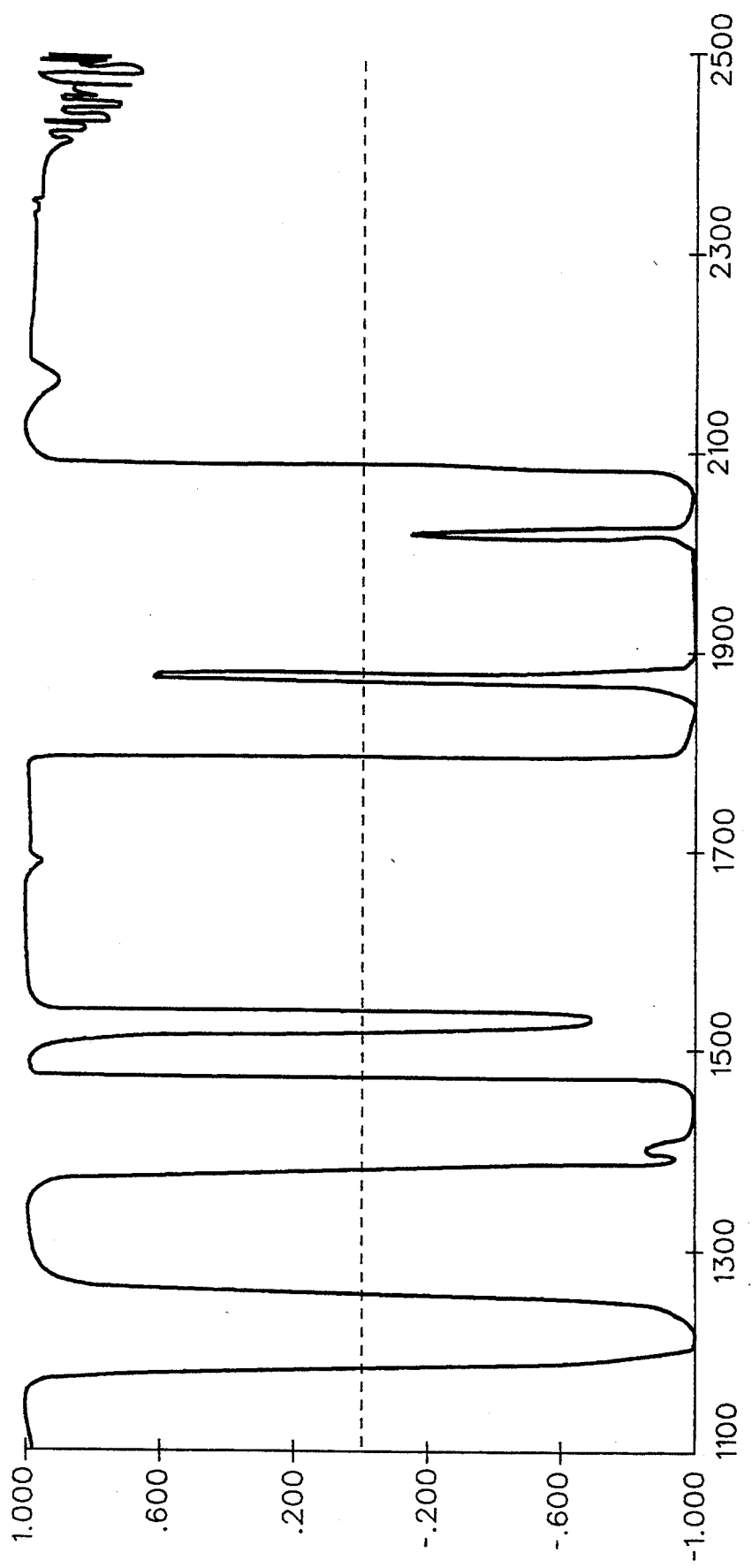
FIG. 9 ORGANIC SULFUR
MULTIPLE CORRELATION vs. WAVELENGTH

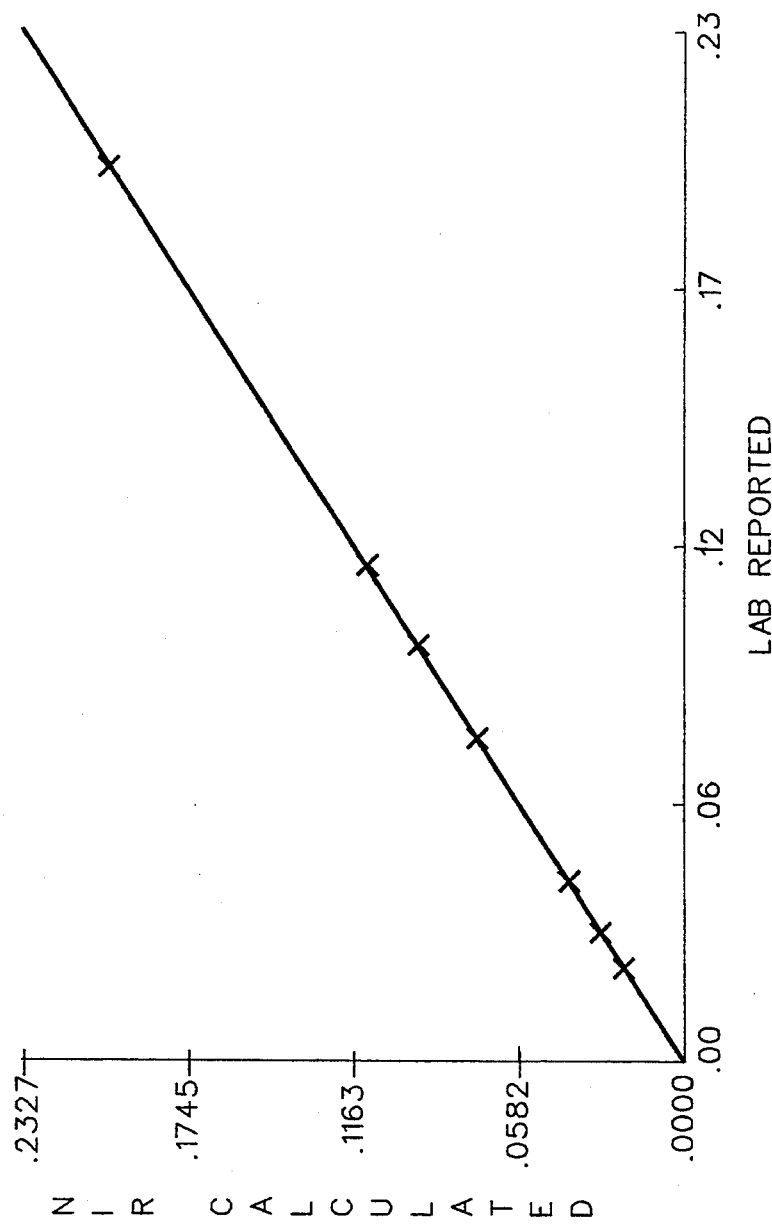

DETERMINATION OF AROMATICS IN HYDROCARBONS BY NEAR INFRARED SPECTROSCOPY

This application is a continuation-in-part of application Ser. No. 839,982 pending, filed Feb. 20, 1992, which is itself a division of U.S. Ser. No. 626,132 filed Dec. 11, 1990, now U.S. Pat. No. 5,145,785.

CROSS REFERENCES TO RELATES APPLICATION

U.S. patent application Ser. No. 506,391, pending filed Apr. 9, 1990 by S. M. Maggard (docket number 6362AUS) relates to the determination of PIANO components in hydrocarbons by near infrared spectroscopy and is therefore related to the field of the present invention.

BACKGROUND OF INVENTION

I. Field of the Invention

The present invention relates to the determination of aromatic and/or organic sulfur and/or color constituents in hydrocarbons by near infrared spectroscopy and is generally classified in U.S. Patent Office Class 250, subclass 343, 341, and 339.

II. Description of the Prior Art

U.S. Pat. No. 4,963,745 granted Oct. 16, 1990 for octane measuring process and device to S. M. Maggard teaches the use of near infrared absorbance of the methyne band to measure octane, etc. of a fuel by near infrared spectroscopy.

The aforementioned U.S. Ser. No. 506,391 teaches the determination of the constituents of PIANO aromatics (paraffins, aromatics, isoparaffins, naphthenes, and olefins) by near infrared techniques.

U.S. Pat. No. 4,880,279, and the references cited thereon, to Hieftje et al. relates to the determination of properties of hydrocarbons by near infrared absorbance.

European Patent Office 2,852,251 filed 10/1988 relates to the general field of analysis by near infrared spectroscopy.

"Near-Infrared Reflectance Analysis by Gauss-Jordan Linear Algebra", D. E. Honigs, J. M. Freelin, G. M. Hieftje, T. B. Hirschreid, Applied Spectroscopy, vol. 37, no. 6, 1983, pp 491–497, teaches statistical manipulation of NIR spectral data.

"Prediction of Gasoline Octane Numbers from Near Infrared Spectral Features in the Range 660–1215 nm" by J. J. Kelly et al., Analytical Chemistry, vol. 61, no. 4, Feb. 15, 1989, pp 313–320, relates to the prediction of octane. Also by Kelly et al., "Nondestructive Analytical Procedure for Simultaneous Estimation of the Major Classes of Hydrocarbon Constituents of Finished Gasolines", Analytical Chemistry, vol. 62, no. 14, Jul. 15, 1990, pp 1444–1451.

Percents of each of the individual compounds detected by gas chromatography are grouped under their respective generic classifications in the PIANO classification system, and the relative percentage of each of the components paraffins through olefins is determined in weight percent, volume percent, or mole percent as required. An example of this procedure is that taught by Analytical Automation Specialists, Inc., "The Detailed Analysis of Petroleum Naphthas, Reformates, Gasoline and Condensates by High-Resolution Gas Chromatography", Operators Manual, P.O. Box 80653, Baton Rouge, La. 70898. Also available is AAS (Analytical Automated Systems) PIANO Software Package, Sievers Research PIANO Software Package.

Other NIR analysis techniques are taught in J. Prakt. Chem., 317(1), 1–16 by Bernhard and Berthold, who perform structural group analysis of mixtures of saturated and aromatic hydrocarbons, and in the quantitative analysis of benzene-toluene-paraffin mixtures in the near-infrared by Leimer and Schmidt in Chem. Tech. (Leipzig), 25(2), 99–100.

"Near-infrared spectroscopy of hydrocarbon functional groups was performed by Tosi and Pinto, Spectrochim ACTA, Part A, 28(3), 585–97, who examined 50 linear and branched paraffins and related the absorbtivities to the concentration of the groups such as $CH_3$ and $CH_2$.

Ultraviolet and near-infrared analysis of mixtures of aromatics is taught by Schmidt in Erdoelkohle, Erdgas, Petrochem., 21(6), 334–40, who sought to determine concentrations of specific compounds.

Kelly, Barlow, Jinguji and Callis of the University of Washington, Seattle, (Analytical Chem. 61, 313–320,) Specialists, Inc., "The Detailed Analysis of Petroleum Naphthas, Refomates, Gasoline and Condensates by High-Resolution Gas Chromatograph", Operators Manual, P.O. Box 80653, Baton Rouge, La. 70898. Also available in AAS (Analytical Automated Systems) PIANO Software Package, Sievers Research PIANO Software Package.

Hydrotreating is taught by many chemical engineering texts. "Reduction of Aromatics in Diesel Fuel" by A. J. Suchanek, National Petroleum Refiners Association, AM-90-21, 1990, provides a brief review.

Other patents which relate to the general field of the invention are U.S. Pat. Nos. 4,277,326; 4,264,336; 3,496,053; 903,020; 4,323,777; 4,433,239; and 4,591,718 and 5,062,976.

Each of the above references is understood to teach a correlation between the absorbance in the near infrared and some physical or chemical property. None of them teach an absolute determination for a very complex mixture such as diesel fuel, as is involved in the percent aromatics determined by the present invention.

Also none of the references teach the determination of aromatics sulfur or color where GC separations are not possible due to co-elution.

SUMMARY OF THE INVENTION

I. General Statement of the Invention

According to the present invention, the absolute concentration of aromatics color and/or sulfur is determined for mixtures with other hydrocarbons, preferably fuels, and most preferably diesel fuels, all grades, kerosene, fuel oils, all grades, light cycle oil, light vacuum oil, heating oils and vacuum oils as known in the petroleum industry. By measuring the absorption at a frequency in the range of 800–2500 nm (nanometers), most preferably from 1650–1700 or 2120–2256 nm, then correcting for the absorption due to non-aromatics in the sample at that frequency and, by data resolution, determining the absolute value of (or percent) aromatics in the sample. The invention can be practiced on a batch basis as in laboratory cells, or by a flow basis, e.g. by using fiber optic or other probes, and can be used for direct or indirect control of process variables such as hydrogen uptake, as illustrated in FIG. 3. Color is measured in the visible range about 400 to 700 nm, using the same or similar spectrophotometer.

Standardization is an important feature of the present invention and is accomplished by separating the aromatics from the non-aromatics in the sample by use of well-known preparative high performance liquid chromatography, e.g. as described in Petroleum Derived Hydrocarbons, John D. Bacha, John W. Newman, and J. L. White, ACS Symposium series 303, Chapter 6.

The concentration of the aromatics in the sample is then determined by measuring the absorbance of each of the two portions at the frequency being used (e.g. 1672 nm) and the absorbance of the aromatic fraction can be (but does not have to be) corrected by subtracting the absorbance of the non-aromatic fraction. The resulting solution of the equation:

$$Y = mX + b + e$$

can be used to determine the percent aromatics of many successive samples so long as the molecular constituents remain approximately the same, thus, for diesel fuel the preferred hydrocarbon mixture to be measured, only one standardization is needed for a long period and many analyses.

In the above equation:
m = the slope of the line (by the standard)
X = the absorbance of the aromatics
b = a constant which is determined by the fitting of the absorbance against the absolute weight values obtained above.
Y = percent aromatics
e = any error in the determination The elements of the invention are therefore preferably the determination of aromatics content in hydrocarbons, preferably in the diesel no. 2 fuel oil boiling range by:

(a) separating the aromatics from the non-aromatics (saturates and olefins) in a representative sample, to be used as a calibrating standard, preferably by preparatory high performance liquid chromatograph ("prep.HPLC");

(b) measuring NIR absorbance of the resulting non-aromatics and aromatic portions (or of prepared known homogenous mixtures) derived from the above sample;

(c) deriving the calibration equation and its constants by Beer-Lambert's Law or other well-known spectral data resolution techniques;

(d) measuring the NIR absorbance of a representative sample using the above calibration equation, determine the aromatic and/or the non-aromatic content.

II. Utility of the Invention

The present invention, as described above, can be utilized for most fuels, preferably for diesel fuel, and preferably by measuring absorbance at a frequency in the range of 800–2500 nm, for aromatics most preferably 1650–1700 nm or 2120–2256 nm for organic sulfur: 850–900, 1118–1162, 1584–1642, 2036–2088, 2110–2152, and/or 2196–2282 nm, and for color: 400–700 nm or same portion thereof. The invention can be utilized as a batch process, in a flow-through cell, by the use of fiberoptic probes either bundled or single fiber, and the process control can be either feed-back or feed-forward based on the samples absorbance in the near-infrared, or optionally the first derivative of the samples absorbance or some other mathematical function of absorbance, being employed e.g. to operate a control valve.

Increasing governmental regulation and environmental laws are impacting the permissible percentage of aromatics tolerated in diesel fuels, turbine fuels, kerosene, heating oils, and other oils.

Therefore, the need for accurate, absolute determinations of the present invention, particularly for on-line control of aromatics in fuels is increasing rapidly.

BRIEF DESCRIPTION OF THE DRAWINGS

FIG. 9 is a plot of multiple correlation vs. wavelength (nm) for organic sulfur.

FIG. 10 is a plot of NIR results vs. ASTM methods D1552 (Leco) and D3120 (microcoulometry) for determination for organic sulfur.

DESCRIPTION OF THE PREFERRED EMBODIMENTS

EXAMPLE 1

(The Invention Using Batch-Type NIR Cells)

A diesel fuel sample (6 grams) is separated into its aromatic and non-aromatic fractions by passing (@500 ml./minute) the fuel down a silica diamine column connected in series to a silica gel column using hexane as the solvent on a Waters Div. Millipore, Milford, Mass., Model 500A high performance liquid chromatograph. The saturate fraction is collected off the end of the column and the hexane mobile phase is removed by rotary evaporation. The aromatics are then back flushed from the column by reversing the flow and substituting methylene chloride as the solvent. The solvent is again removed by rotary evaporation.

The near infrared absorbance spectra of the non-aromatic and aromatic fractions (or known proportions thereof) are measured on an NIR Systems, Inc., Model 6500 spectrophotometer at 1672 nm and assigned concentrations of 0% and 100% aromatics by weight, respectively.

An equation of the form $Y = mX + b$ is calculated from Beer-Lambert Law, where Y is the aromatic concentration, X is the absorbance, m is the slope of the regression line, and b is its Y-intercept.

Figure 7:
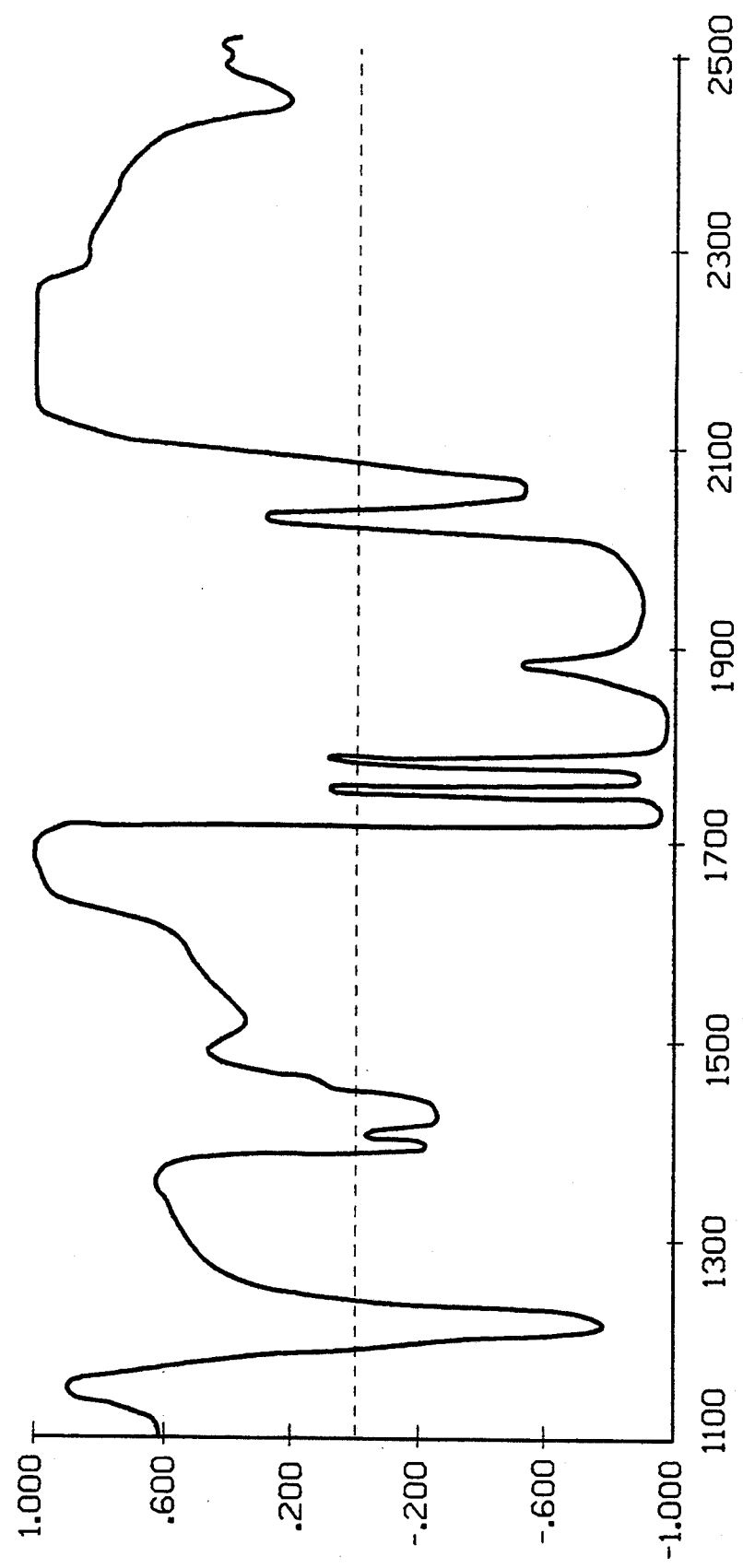
FIG. 7 is a plot showing the correlation observed at each wavelength from 1100–2500 nm for the aromatic content of diesel fuels using the techniques of the current invention. Note the superior correlation discovered at 1650 to 1700 nm and at 2120 to 2256 nm, most preferably 1654 to 1696 nm, or 2124 to 2252 nm, or both.
Figure 8:
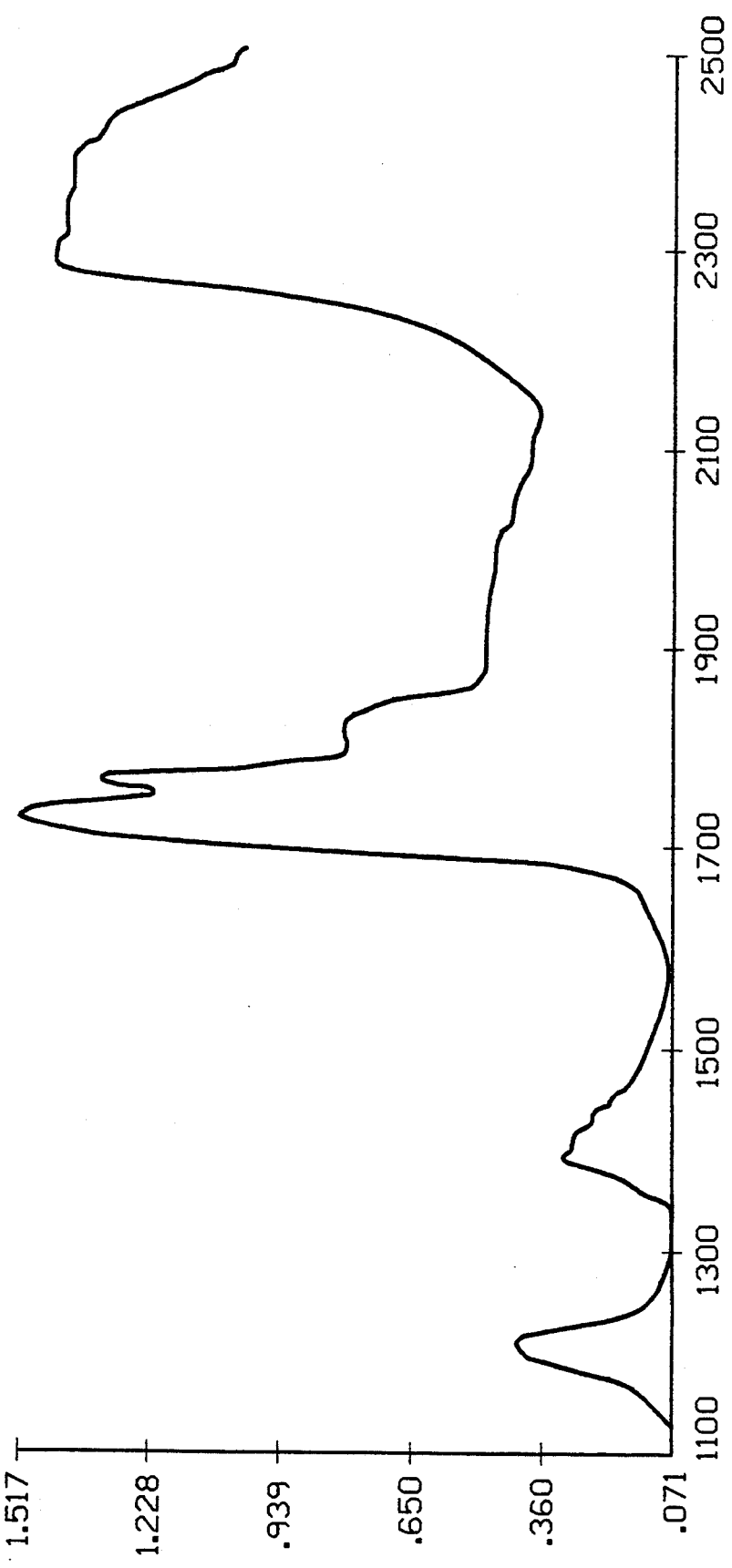
FIG. 8 is a near infrared (NIR) absorbance spectrum of the non-aromatic fraction of diesel fuel which was obtained by HPLC.

The absorbances of a series of five unknown diesel fuel samples are measured and, using the above equation and the sample's absorbance at 1672 nm, aromatic concentration of each sample is calculated and the correlations are plotted together as FIG. 7. Note the near perfect correlation in the preferred bands of the invention.

EXAMPLE 2

(Flow-Through Mode)

When the techniques of Example 1 are employed using fiberoptic probes to measure flowing streams and side streams in a refinery diesel fuel stream, accuracy approximately as good as obtained in the batch-process of Example 1 is achieved. Fiber optical probes preferably use the NIR range of 1650 and 1700 nm because of the cost and difficulty in obtaining non-absorbing fiber probes which transmit in the range of 2124 to 2252 nm.

EXAMPLE 3

(The Invention Controlling a Process)

Figure 1:
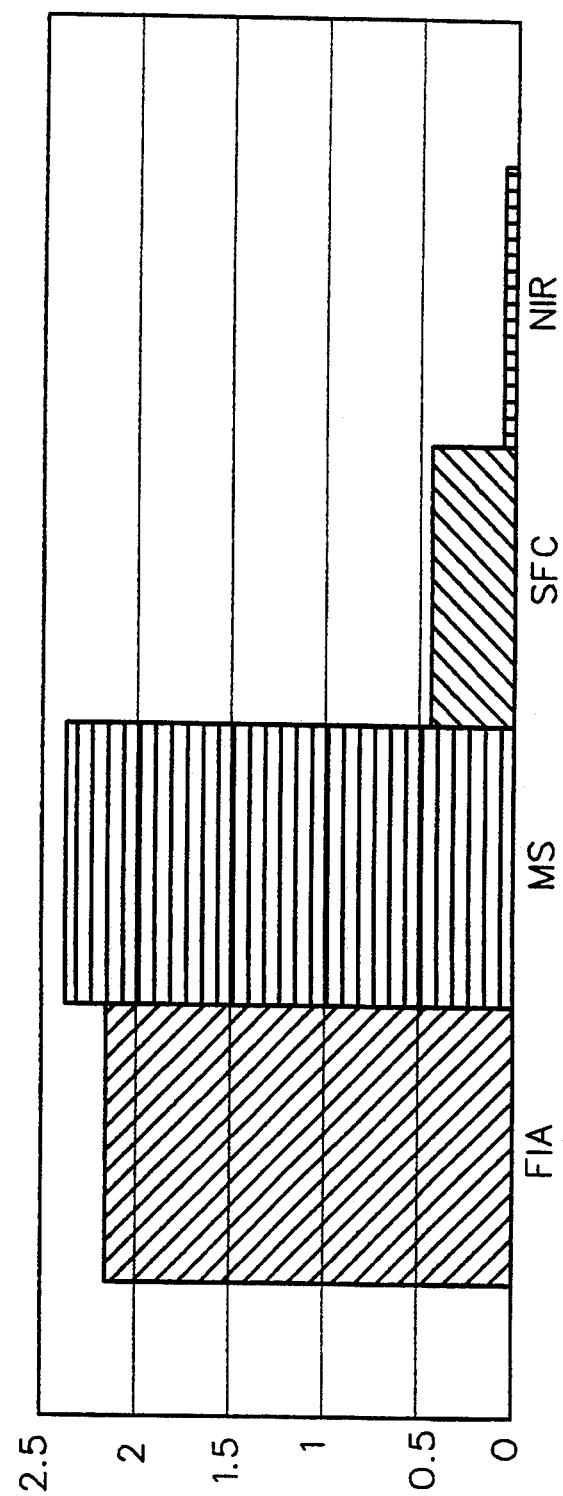
FIG. 1 is a comparison of the repeatability error (% by absolute error) of four analytical methods for determining aromatics in diesel fuels (no. 2 fuel oil). The methods compared are fluorescent indicator absorption (FIA) by ASTM D-1319; mass spectroscopy (MS); super fluid chromatography (SFC) in which $CO_2$ above its critical pressure and temperature is used as the eluent; and near infrared according to the techniques of the present invention (NIR) for sets of 6 identical samples. This figure shows the excellent repeatability of the techniques of the present invention. (All determinations are in wt. % except FIA is in vol. %.)
Figure 2:
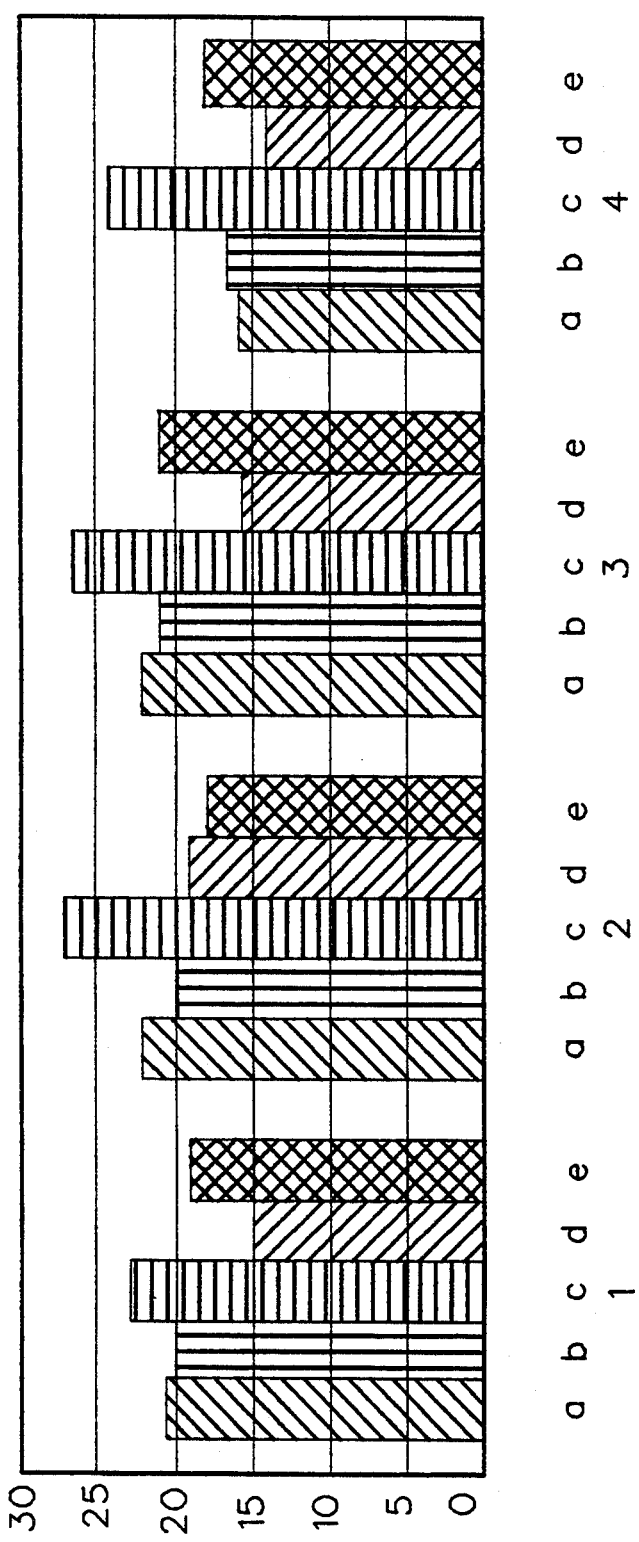
FIG. 2 is a comparison of the percent aromatics determined in identical sets of 4 samples by heated FIA (a), heated FIA plus water deactivation of the chromatographic column (b), SFC (c); HPLC/DCD (high performance liquid chromatography using a dielectric constant-measuring detector) (d); and the NIR of the present invention (e). Note that results are expressed in volume percent for the two FIA methods and the HPLC/DCD method, whereas SFC and NIR results are expressed in weight percent. Note that NIR (except in sample no. 2) is closest to the average of all methods combined.
Figure 3:
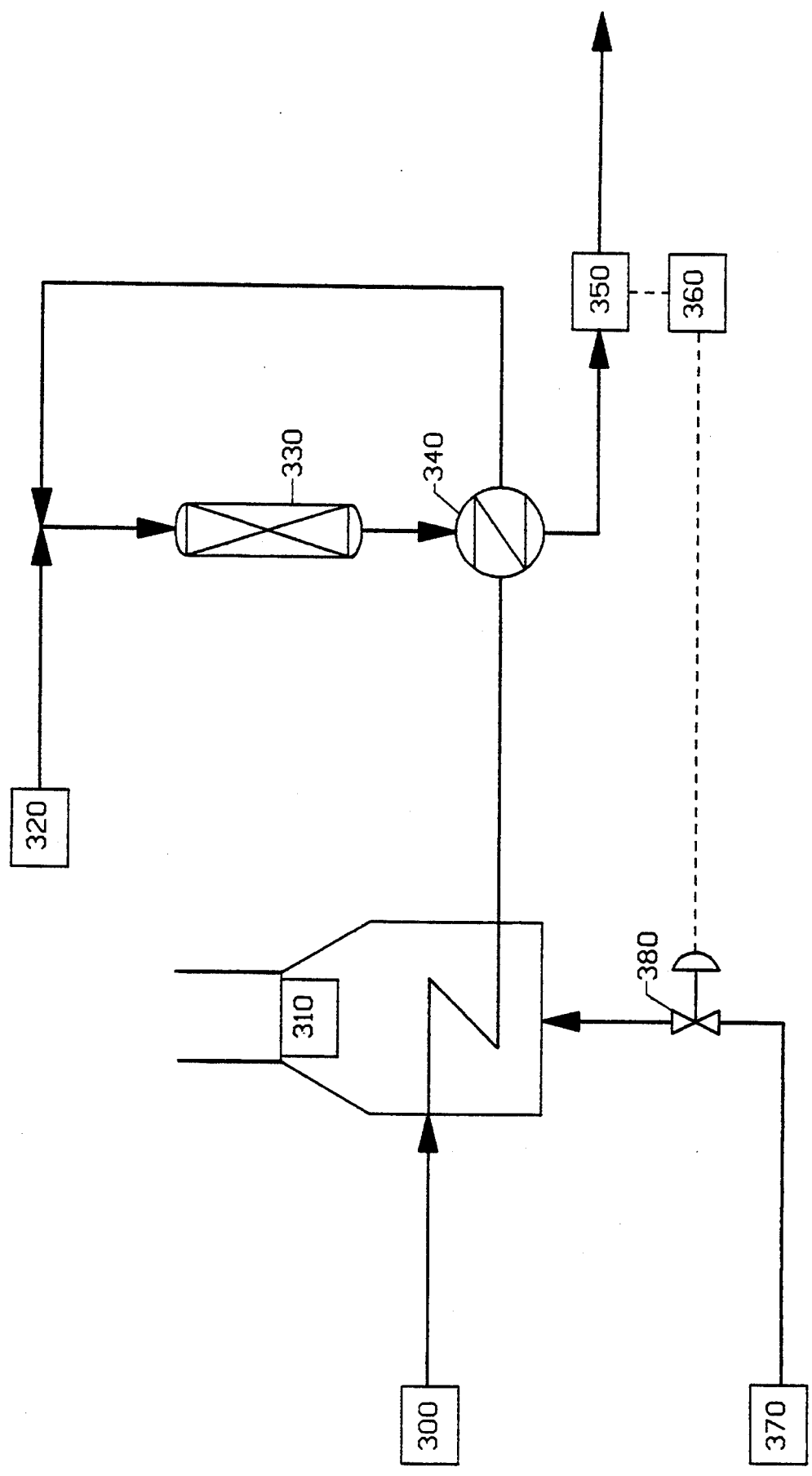
FIG. 3 is a schematic diagram of a control system utilizing the NIR techniques of the present invention to control a refinery hydrogenation unit in which sufficient hydrogen is added not only to combine with the sulfur, but also sufficient to cause scisson and destruction of aromatics in diesel fuel.

FIG. 3 schematically shows an important process control application of this invention. New diesel fuel regulations require that highway fuel produced after October, 1993, meet a maximum sulfur content specification. An NIR instrument calibrated as according to this invention, very close control of hydrotreater operation can be attained at minimum severity and hydrogen consumption. Raw feed, stream 300, flows through fired heater 310, feed/effluent exchanger 340, is admixed with hydrogen stream 320, through an adiabatic hydrotreating reactor 330, to tankage. The absorbance spectrum of the stream is measured by NIR probe 350, and this information provided to the process control computer 360. Conversion of spectrum to estimated sulfur content is made by the computer, and the flow of fuel stream 370 to the fired heater is adjusted as necessary by control valve 380. This on-line control allows rapid, very close control of product quality and eliminates present problems with production of off-spec finished products in quantities because corrections are implemented much sooner. This also results in a close-specification diesel fuel which is in much demand in today's marketplace.

EXAMPLE 4

(Controlling Hydrotreater Severity)

Figure 5:
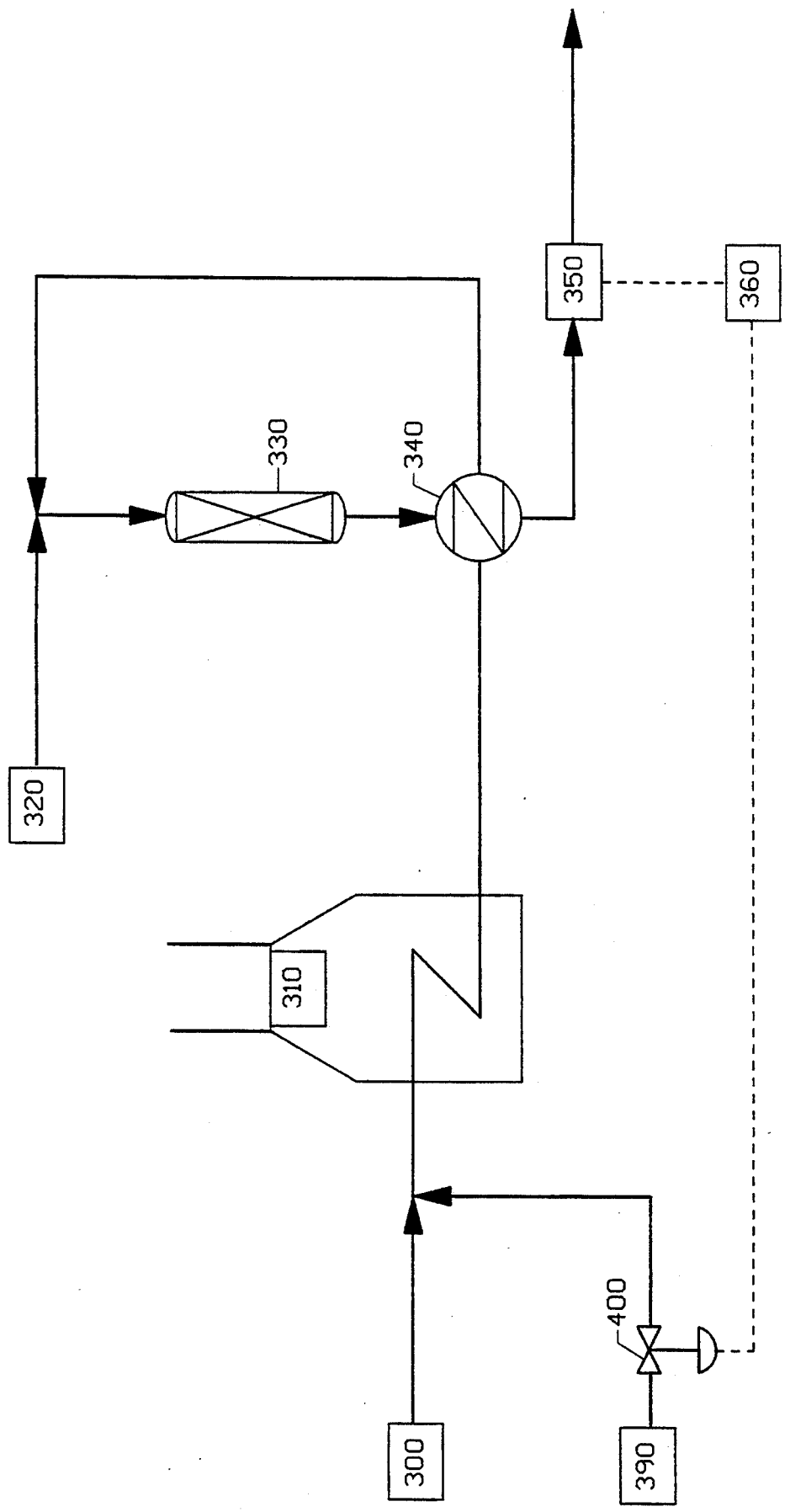
FIG. 5 shows a schematic control system as detailed in Example 4.
Figure 6:
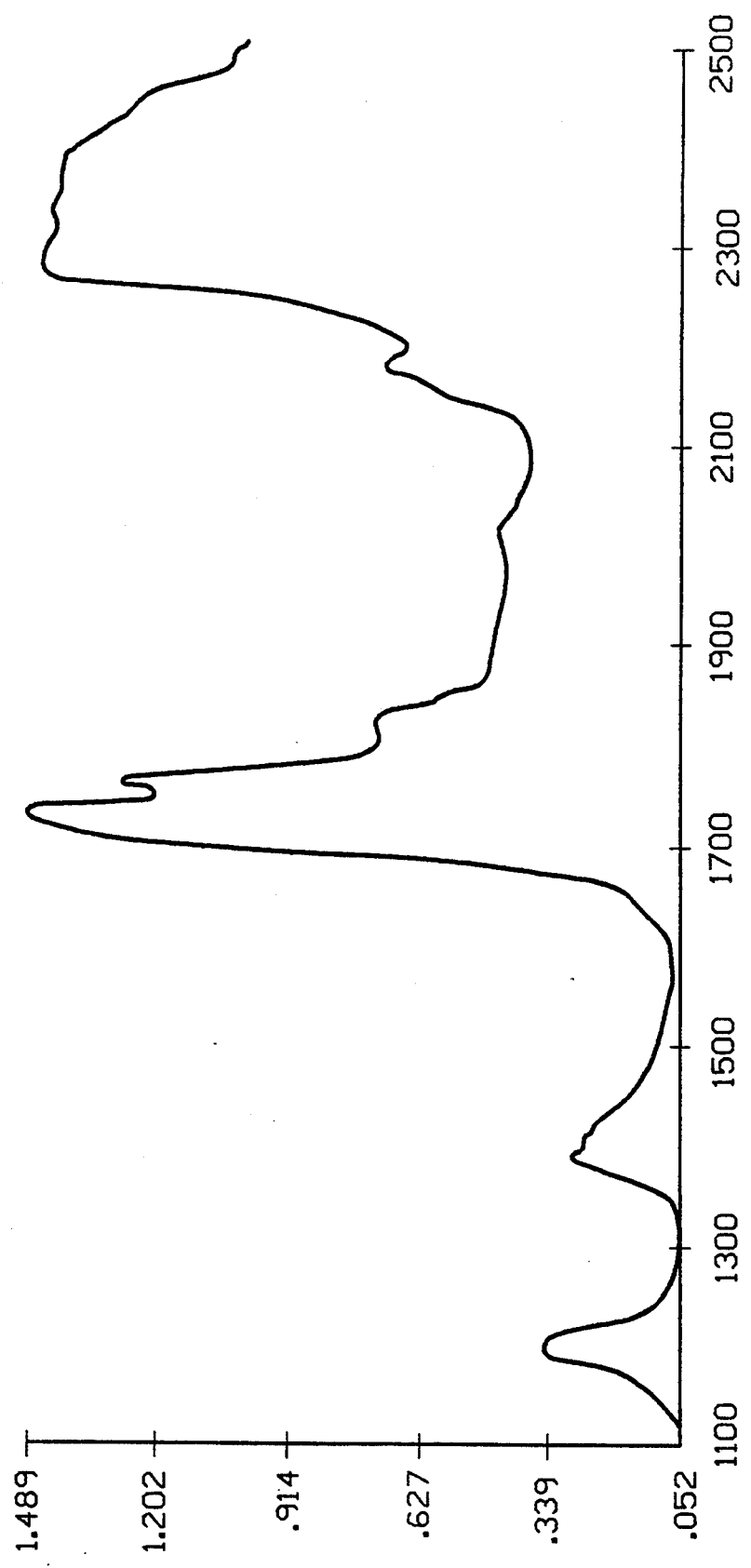
FIG. 6 is a near infrared absorbance spectrum of a typical diesel fuel.

Additional process control advantages of the invention are exemplified in FIG. 5. For the same hydrotreating scheme shown in FIG. 3 (Example 3), this invention can allow maximum use of aromatic components in diesel fuel such as FCC LCO while operating the hydrotreater at maximum severity when aromatic/cetane limits are reached. Maximum use of FCC LCO (light cycle oil, high in aromatics) in diesel is advantageous to the refiner due to its relatively low value, but it is a major contributor to the aromatics content of the diesel pool. In FIG. 5, on-line NIR analysis allows maximum FCC LCO flow by maintaining constant analysis of the product diesel stream, providing information to the aforementioned process control computer 360 which adjusts FCC LCO flow 390 through flow control valve 400 such that the product stream just meets the required aromatics/cetane specification. This application is particularly attractive in that hydrotreating catalyst deactivation will be automatically compensated by the control loop by reducing the quantity of FCC LCO blended as the catalyst activity declines over the normal aging cycle.

EXAMPLE 5

(Control of Aromatics in Solvents)

Manufacture of Low Odor Base Solvent (LOBS) is accomplished by the control schematic of FIG. 3. An NIR probe, properly calibrated for 0–5% aromatics, is used to directly control product quality (low aromatic content) to meet the specification level, by hydrotreatment. Blending also can be controlled by NIR, preferably using feed-forward of the aromatics content of the feed as measured by NIR.

EXAMPLE 6

(The Invention Controlling Desulfurizing by Hydrotreating)

Figure 4:
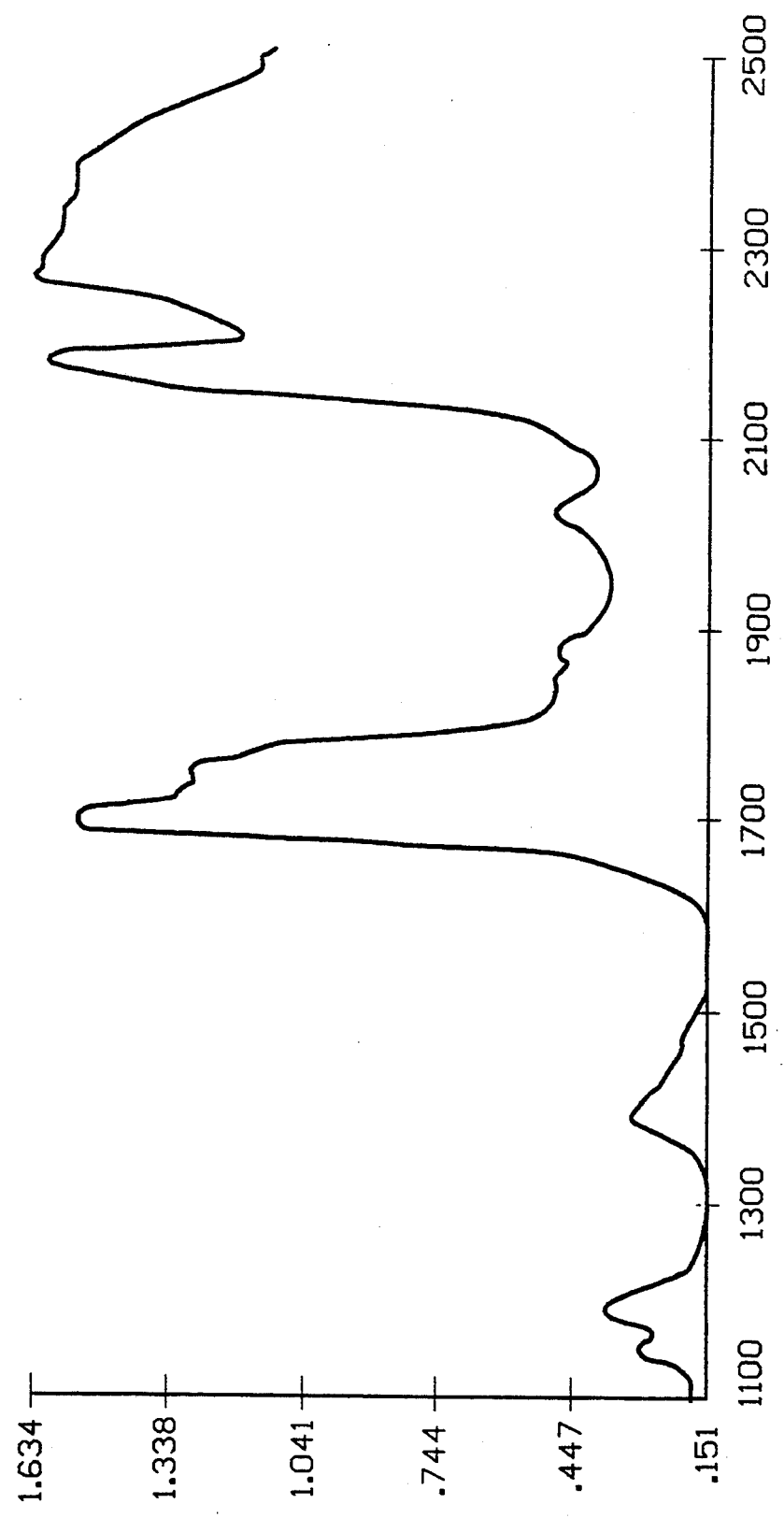
FIG. 4 is a near infrared absorbance spectrum of the aromatic fraction of a diesel fuel which was obtained by HPLC.

Using the same apparatus and using methods similar to those of FIGS. 3 and 4, the invention is used to control the sulfur in the final product diesel fuel existing from a hydrotreater using feed-back (feed-forward can be used to substitute for feedback or both feed-back and feed-forward control systems can be used, utilizing the invention as the primary sensor or sulfur).

Recent U.S. government regulations will require a maximum of 0.05 wt. % sulfur in diesel fuels, so removal of sulfur by hydrotreating and close control to avoid excess consumption of hydrogen or off-spec high-sulfur diesel fuel have become increasingly critical to the refining industry.

An important feature of the invention is the discovery that sulfur, at least predominantly, is usually present in diesel fuel and heavier hydrocarbons as a derivative of benzothiophene. Surprisingly, the C:S band of these thiophene or similar aromatic molecules can be observed by the NIR spectra of the present invention, despite the expectation that C:S would give a weak signal in comparison to C:H, due to the relative similarity of the carbon and sulfur molecular weights. Since there may be other aromatics present, e.g. mono, di, and tri aromatics, the ratio of aromatics to sulfur in any given petroleum feedstock, e.g. diesel fuel, can vary substantially because some of the aromatics will contain sulfur and is primarily present as derivatives of benzothiophene, a correlation can be made between the sulfur content and the aromatic content for any given feedstock.

Showing this, the techniques of measuring and controlling sulfur are essentially the same as those utilized in Example 4 for controlling aromaticity by the invention.

Once the ratio of total aromatics to benzothiophenes is known for each of the different feedstocks to be handled, measuring the aromatic content of the individual feedstock and applying the relationship between aromatics and thiophenes can be used to give a reliable measure of the sulfur content of a blended product.

The invention can alternatively be used to directly compute the sulfur contained in each individual feedstock, or in the product if feed-back is being used, by monitoring the sulfur band itself which appears between 1584 and 1642 nm, and in some instances in the region 2036–2282 nm. As shown in FIG. 9, this is a region where there is also almost perfect correlation with aromatic content. Thus, through there may be a distinct sulfur band in the 2036–2282 region, it appears that it is interfered with by the strong aromatic band, but this is not yet determined due to the difficulty in band assignments.

There is a second overtone of the benzothiophene absorption band at about 1100–1150 nm, and a third overtone at about 850–900 nm, and these can be used, either directly or by mathematical conversion to provide a measure of sulfur in diesel fuels and heavier hydrocarbon streams, through these overtones may also sulfur from the aromatic combination band interference. There may well be distinct sulfur bands in the primary, secondary and tertiary overtone combination regions. A combination of the primary band and these overtones may, in some instances, be valuable for analytical measurement of sulfur.

Referring to FIG. 5, on-line NIR analysis in the benzothiophenic band determines sulfur in the product diesel oil stream, providing information to the process control computer 360 which adjusts FCC LCO flow 390 through flow control valve 400 so that the product stream just meets the required maximum sulfur specification. As with aromatics control, this application is particularly attractive because the hydrotreating catalyst's gradual deactivation will be automatically compensated for by the control loop reducing the quantity of FCC LCO fed to the unit. Preferably, with sulfur, we have found wavelengths in the ranges 850–900 1118–1162, 1584–1642, 2036–2088, 2110–2152, or 2196–2282 nm to be analytically useful for determining sulfur content.

The statistical method is more fully set forth in Example 7.

EXAMPLE 7

(Statistical Method for the Determination of Sulfur in Diesel)

Table A shows calibration results by forty samples which include one feed sample and 39 samples that have been hydrotreated at different severity. These samples span a diesel range of from 0.015 to 1.016 wt. % sulfur in diesel fuel. Sulfur was first determined by analysis by a Leco Sulfur Analyzer using ASTM D1552 procedure for high sulfur samples, and for low sulfur samples, sulfur was determined by a Dohrmann sulfur Microcoulometer using analytical procedures of ASTM D3120. These results are listed in Table A under "Lab %". Using the data of Table A, a correlation is developed against the laboratory test data. The NIR absorptions are measured and correlated using the wavelengths of 1620 nm, an analytical waveguide for benzothiophenic sulfur, and 2120 nm, combination band for aromatic and/or sulfur. A correlation "multiple R" of 0.9935 is obtained. That is an excellent correlation and is further confirmed by the regression constant K(0) equalling −0.177, remarkably close to 0, indicating a near absence of analytical interference. Similar results are obtained with diesel fuel, jet fuel, kerosene, lube oil, and FCC feedstock.

TABLE A

| | NIRSystems Calculated Percents | | |
|---|---|---|---|
| Spl No. | Lab % | NIR % | Residual |
| 1 | 1.016 | 1.006 | −.010 |
| 2 | .243 | .225 | −.018 |
| 3 | .172 | .160 | −.012 |
| 4 | .089 | .085 | −.004 |
| 5 | .051 | .035 | −.016 |
| 6 | .023 | .038 | .015 |
| 7 | .105 | .073 | −.032 |
| 8 | .030 | .055 | .025 |
| 9 | .035 | .056 | .022 |
| 10 | .027 | .039 | .012 |
| 11 | .255 | .276 | .021 |
| 12 | .159 | .174 | .015 |
| 13 | .157 | .155 | −.002 |
| 14 | .110 | .099 | −.011 |
| 15 | .079 | .057 | −.023 |
| 16 | .166 | .141 | −.025 |
| 17 | .074 | .082 | .008 |
| 18 | .075 | .081 | .006 |
| 19 | .078 | .086 | .009 |
| 20 | .056 | .085 | .029 |
| 21 | .349 | .363 | .014 |
| 22 | .236 | .271 | .035 |
| 23 | .193 | .189 | −.004 |
| 24 | .139 | .155 | .016 |
| 25 | .079 | .063 | −.016 |
| 26 | .201 | .169 | −.032 |
| 27 | .081 | .087 | .006 |
| 28 | .078 | .084 | .006 |
| 29 | .077 | .087 | .011 |
| 30 | .052 | .071 | .019 |
| 31 | .235 | .219 | −.016 |
| 32 | .096 | .108 | .012 |
| 33 | .074 | .068 | −.006 |
| 34 | .068 | .045 | −.023 |
| 35 | .036 | −.003 | −.039 |
| 36 | .100 | .077 | −.023 |
| 37 | .030 | .035 | .005 |
| 38 | .028 | .026 | −.003 |
| 39 | .023 | .027 | .003 |
| 40 | .015 | .040 | .025 |

EXAMPLE 8

(The Invention Using Batch-Type NIR Cells for Sulfur Determination)

A diesel fuel sample (6 grams) is separated into high sulfur and low sulfur fractions by passing (@500 ml./minute) the fuel down a silica diamine column connected in series to a silica gel column using hexane as the solvent on a Waters Div. Millipore, Milford, Mass., Model 500A high performance liquid chromatograph. The low sulfur fraction is collected off the end of the column and the hexane mobile phase is removed by rotary evaporation. The high sulfur fraction is then back flushed from the column by reversing the flow and substituting methylene chloride as the solvent. The solvent is again removed by rotary evaporation.

The high sulfur and low sulfur fractions are mixed in known proportions to prepare 7 known standards containing 0.023–0.201 wt. % sulfur.

The near infrared absorbance spectra of the 7 known standard fractions (or known proportions thereof) are measured on an NIR Systems, Inc., Model 6500 spectrophotometer at 2128 nm using their known concentrations as the dependent variable. Alternatively, we have found it acceptable to substitute a derivative of the absorbance spectra for the absorbance spectra. A plot of the correlation with sulfur versus wavelength is shown in FIG. 9 and the calibration plot (actual sulfur vs. predicted sulfur) is shown in FIG. 10.

An equation of the form Y=Mx+b is calculated from Beer-Lambert Law, where Y is the sulfur concentration, X is the samples absorbance at 2128 nm, m is the slope of the regression line, and b is its Y-intercept. A correlation of 0.9999 and a standard error of 0.0011 wt. % sulfur is obtained during the calibration using the Beer-Lambert Law.

The absorbances of a series of 39 unknown diesel fuel samples are measured and, using the above equation and the sample's absorbance at 2128 nm, the sulfur concentration of each sample is calculated. Note the near perfect correlation with sulfur content in the preferred bands of the invention for the calibration data.

EXAMPLE 9

(Measuring ASTM Color)

A series of color standards are prepared by visually matching a series of diesel fuel samples diluted with paraffin oil to the visual color standards used in ASTM D1500 to determine ASTM Color. The colors ranged from 1.0–5.5 in increments of 0.5. The liquid visual standards produced in this manner were correlated against their visible absorbance spectra at 594 and 500 nm. The correlation coefficient obtained was 0.999 with a standard error of 0.075. The agreed quite well with the 0.5 intervals which were determined by the primary test method and gave correct test results when measured on 39 unknown test samples.

MODIFICATIONS

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the invention disclosed herein.

Reference to documents made in the specification is intended to result in such patents or literature being expressly incorporated herein by reference including any patents or other literature references cited within such documents.

What is claimed is:

1. A process for controlling organic sulfur content of a hydrocarbon product comprising in combination:
   a. measuring the near infrared absorbance of a hydrocarbon in the range of 1600–1650, 1100–1150, 850–950 or 2050–2200 nm, and providing a signal indicative of said absorbance or a mathematical function thereof;
   b. controlling a sulfur-removal process or a blending process by operating control means responsive to said signal for varying the organic sulfur content of said hydrocarbon product by said sulfur-removal process or by said blending process with additional hydrocarbons having a different organic sulfur content.

2. A process according to claim 1 wherein said sulfur removal process comprises hydrotreating.

3. A process according to claim 1 wherein said hydrocarbon comprises a flowing stream of hydrocarbon comprising 0.001 to 5 wt. % organic sulfur compounds.

4. A process according to claim 1 wherein said hydrocarbon comprises kerosene or diesel fuel.

5. A process according to claim 1 wherein said hydrocarbon comprises lube oil.

6. A process according to claim 1 wherein said mathematical function comprises a derivative.

7. A process according to claim 1 for controlling organic sulfur content of hydrocarbons by near infrared spectrophotometer comprising in combination the steps of:
   a. selecting a sample generally representative of said hydrocarbons;
   b. separating out at least a known percentage of the organic sulfur in said sample from the sulfur portion of said sample;
   c. measuring the absorbance of the aromatics portion and the non-aromatics portion or a portion containing known mixed proportions of aromatics, and/or saturates, and/or olefins, in the range of 700–2500 nm;
   d. by Beer-Lambert's Law or other methods of data resolution, calibrating the near infrared spectrophotometer or related computer receiving a signal from the spectrophotometer to provide a signal indicative of the concentration of sulfur in at least one additional hydrocarbon sample,
   e. operating control means responsive to said signal for varying the organic sulfur content of said hydrocarbon by sulfur-removal process or blending with additional hydrocarbons having a different organic sulfur content.

8. A process according to claim 7 in which NIR is measured by a near infrared spectrophotometer which has been calibrated by the statistical correlation technique by another primary test method result, said other primary test method being selected from the group consisting of Pyrolizer sulfur analyzer, microcoulometer, x-ray defraction.

9. A process according to claim 1 wherein said signal is processed by a computer which emits a process signal to said control means to control said process to achieve the desired sulfur value in said finished hydrocarbon.

10. A process for decreasing sulfur concentration by controlling a hydrotreating process in which at least one parameter of hydrotreating severity selected from the group consisting of increasing temperature, decreasing throughput, increasing pressure and increasing hydrogen rate is controlled by control means responsive to near infrared (NIR) measurement of sulfur of sulfur-containing heterocyclic compounds in the effluent from said hydrotreating process.

11. A process for controlling the color of hydrocarbons containing color-imparting compounds by near infrared spectrophotometry comprising in combination the steps of:
   a. measuring absorbance in the visible portion of the spectrum, about 400–700 nm;
   b. by Beer-Lambert's law or other methods of data resolution, calibrating the near infrared spectrophotometer or related computer receiving a signal from the spectrophotometer to provide a signal indicative of the color of said hydrocarbon; and
   c. controlling the color of the hydrocarbons by imputing said signal to control means for controlling a process which varies the color of said hydrocarbons by adsorption, by blending with hydrocarbons having different color or by hydrotreating, or by other color modifying process to provide a hydrocarbon product having a color within desired values.

12. A process according to claim 11 wherein the process for controlling color comprises adsorption onto a solid adsorbent which preferentially adsorbs color-imparting moieties.

13. A process for controlling organic sulfur content of hydrocarbon using apparatus comprising a near infrared spectrophotometer and control means responsive to signals, said process comprising in combination:
   a. calibrating said spectrophotometer by:
      1. selecting a sample of known organic sulfur content generally representative of said hydrocarbons;
      2. measuring the near infrared absorption of said sample in the range of 700–2500 nm;
      3. controlling organic sulfur content of said hydrocarbon by correlating said absorbance with said organic sulfur content by Beer-Lambert's law or other methods of data resolution to provide a calibration equation so that the near infrared spectrophotometer or related computer receiving a signal from the spectrophotometer provides an output signal indicative of the concentration of sulfur in at least one additional hydrocarbon sample;
   b. determining the organic sulfur content of at least one unknown hydrocarbon by:
      1. measuring the absorption of said unknown stream of hydrocarbon sample;
      2. applying the calibration equation determined above, to provide a signal indicative of the concentration of organic sulfur in said unknown stream of hydrocarbons; and
   c. controlling the sulfur content of said unknown stream by: operating control means responsive to said output signal for varying the organic sulfur content in said hydrocarbon by sulfur-removal process, or by blending with additional hydrocarbons having a different organic sulfur content, to achieve a desired organic sulfur content in said unknown hydrocarbon stream.

14. A process according to claim 13 wherein said absorbance is measured in the range of 850–900 nm.

15. A process according to claim 13 wherein said absorbance is measured in the range of 1118–1162 nm.

16. A process according to claim 13 wherein said absorbance is measured in the range of 1584–1642 nm.

17. A process according to claim 13 wherein said absorbance is measured in the range of 2036–2088 nm.

18. A process according to claim 13 wherein said absorbance is measured in the range of 2110–2152 nm.

19. A process according to claim 13 wherein said absorbance is measured in the range of 2196–2282 nm.

20. A process according to claim 13 wherein the mathematical function comprises taking the derivative.

21. A process for controlling organic sulfur content of hydrocarbons comprising in combination:
   a. measuring the near infrared absorbance of said hydrocarbon in the range of 700–2500 nm and statistically correlating at least one wavelength in 850–2285 nm to the organic sulfur content measured by a primary test method; and providing a signal indicative of said absorbance or a mathematical function thereof;
   b. controlling a sulfur-removal process or a blending process by operating control means responsive to said signal for varying the organic sulfur content of said hydrocarbon by sulfur-removal process or blending with additional hydrocarbons having a different organic sulfur content; to achieve a desired organic sulfur content in the finished hydrocarbon product.

22. A process according to claim 21 wherein said absorbance is measured in the range of 850–900 nm.

23. A process according to claim 21 wherein said absorbance is measured in the range of 1118–1162 nm.

24. A process according to claim 21 wherein said absorbance is measured in the range of 1584–1642 nm.

25. A process according to claim 21 wherein said absorbance is measured in the range of 2036–2088 nm.

26. A process according to claim 21 wherein said absorbance is measured in the range of 2110–2152 nm.

27. A process according to claim 21 wherein said absorbance is measured in the range of 2196–2282 nm.

28. A process according to claim 21 wherein the mathematical function comprises taking the derivative.

29. A process for controlling the organic sulfur content of hydrocarbons using a near infrared spectrophotometer comprising in combination the steps of:
   a. selecting a sample of known organic sulfur content generally representative of said hydrocarbons;
   b. separating out a non-aromatics portion from an aromatics portion which will be higher in organic sulfur than said non-aromatic hydrocarbon portion of said sample;
   c. measuring the absorbance of said aromatics portion and said non-aromatics portion or a portion containing known mixed proportions of aromatics, and/or saturates, and/or olefins, in the range of 1650–1700 or 2120–2256 nm;
   d. by Beer-Lambert's Law or other methods of data resolution, calibrating said near infrared spectrophotometer or a related computer receiving a signal from the spectrophotometer to provide a signal indicative of the concentration of aromatics, or non-aromatics, in at least one additional hydrocarbon sample;
   e. thereafter measuring the absorbance of the same or a different hydrocarbon sample with said calibrated spectrophotometer in at least one of said ranges; and
   f. determining aromatics content of said same or different sample from its absorbance,
   g. controlling the organic sulfur content of said hydrocarbon by means responsive to said aromatics content as determined in step f.

30. A process according to claim 29 wherein said absorbance is measured in the range of 850–900 nm.

31. A process according to claim 29 wherein said absorbance is measured in the range of 1118–1162 nm.

32. A process according to claim 29 wherein said absorbance is measured in the range of 1584–1642 nm.

33. A process according to claim 29 wherein said absorbance is measured in the range of 2036–2088 nm.

34. A process according to claim 29 wherein said absorbance is measured in the range of 2110–2152 nm.

35. A process according to claim 29 wherein said absorbance is measured in the range of 2196–2282 nm.

36. A process according to claim 29 wherein the mathematical function comprises taking the derivative.

* * * * *